(12) United States Patent
Lipscomb

(10) Patent No.: US 10,471,246 B1
(45) Date of Patent: Nov. 12, 2019

(54) WIRELESS POWER SUPPLY AND SPEED CONTROLLER FOR TATTOO MACHINE

(71) Applicant: Randy Lipscomb, Louisville, KY (US)

(72) Inventor: Randy Lipscomb, Louisville, KY (US)

( * ) Notice: Subject to any disclaimer, the term of this patent is extended or adjusted under 35 U.S.C. 154(b) by 0 days.

(21) Appl. No.: 16/417,904

(22) Filed: May 21, 2019

Related U.S. Application Data

(60) Provisional application No. 62/750,254, filed on Oct. 25, 2018.

(51) Int. Cl.
*A61M 37/00* (2006.01)
*H02J 7/00* (2006.01)

(52) U.S. Cl.
CPC ....... *A61M 37/0076* (2013.01); *H02J 7/0042* (2013.01); *H02J 7/0052* (2013.01); *A61M 2205/33* (2013.01); *A61M 2205/8206* (2013.01); *A61M 2205/8237* (2013.01); *A61M 2205/8262* (2013.01); *H02J 2007/0062* (2013.01)

(58) Field of Classification Search
CPC .............................................. A61M 37/0076
See application file for complete search history.

(56) References Cited

U.S. PATENT DOCUMENTS

| | | | |
|---|---|---|---|
| 6,550,356 B1 * | 4/2003 | Underwood | A61M 37/0084 30/362 |
| 10,220,196 B2 | 3/2019 | Johansson | |
| 2010/0072827 A1 * | 3/2010 | Norstrom | H01M 2/1022 307/112 |
| 2010/0241151 A1 * | 9/2010 | Rickard | A61M 37/0076 606/186 |
| 2012/0024114 A1 | 2/2012 | Vazquez | |
| 2018/0043146 A1 * | 2/2018 | Vescovi | A61M 37/0084 |

FOREIGN PATENT DOCUMENTS

WO   WO 2017/194336 A1   11/2017

* cited by examiner

*Primary Examiner* — Jared Fureman
*Assistant Examiner* — Fritz M Fleming
(74) *Attorney, Agent, or Firm* — Dale J. Ream

(57) ABSTRACT

A wireless power supply and voltage controller for powering and controlling a tattoo machine according to the present invention includes a battery housing having a plurality of walls that, collectively, define an interior area and a rechargeable battery positioned in the interior area of the battery housing. An input selection assembly is positioned on an exterior surface of a respective wall of the plurality of walls of the battery housing, the input selection assembly being operable to generate a speed generation signal. A controller is electrically connected to the input selection assembly that is operable to regulate a quantity of voltage flowing from the battery according to the speed generation signal.

5 Claims, 4 Drawing Sheets

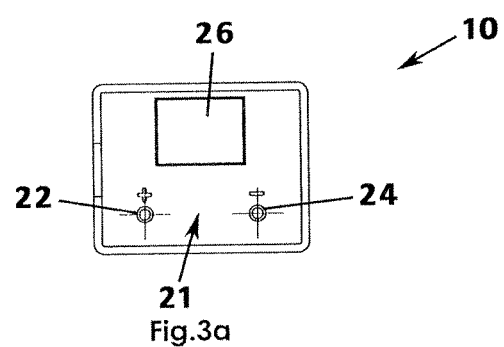
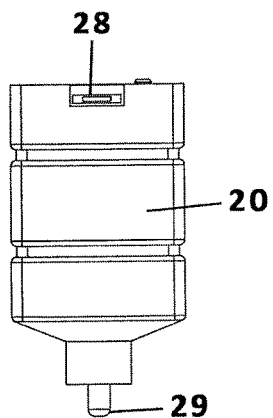
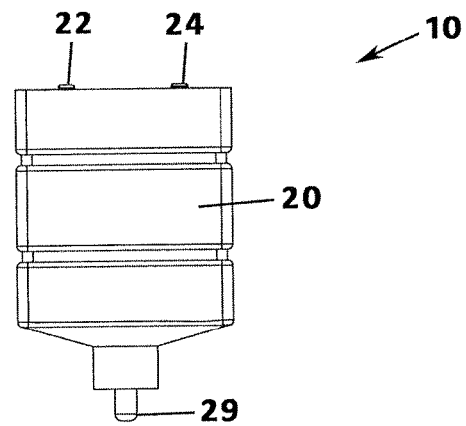
Fig.3c  Fig.3b

US 10,471,246 B1

WIRELESS POWER SUPPLY AND SPEED CONTROLLER FOR TATTOO MACHINE

REFERENCE TO RELATED APPLICATIONS

This application claims the priority of provisional patent application U.S. Ser. No. 62/750,254 filed Oct. 25, 2018 and titled Wireless Power Supply and which is incorporated herein in its entirety.

BACKGROUND OF THE INVENTION

This invention relates to an accessory for use with a tattoo device and, more particularly, to a power supply removably and electrically coupled to the tattoo device that includes input controls for raising and lowering an amount of electrical current delivered to a motor of the tattoo device, the selected voltage setting of causes the tattoo motor to operate accordingly.

A tattoo machine is a handheld tool that utilizes electromagnetic coils, needle, and ink to create a permanent marking, referred to as a tattoo, on the skin of a person. Tattoos have become very popular in mainstream America and, in fact, a complete industry has been created to supply the demand to "ink" the skin of customers. A tattoo machine includes a motor to actuate movement of functional elements and, accordingly, must include or be electrically connected to an electrical power supply. Historically, a tattoo machine is connected to AC power such as a wall socket via power cable or may include a rechargeable battery that must be connected to a separate base unit for power or during use.

Although presumably effective for their intended use, it is inconvenient and even bothersome to have a power cable that gets in the way between the machine and a customer's skin during use or to have collateral charging equipment between uses.

Therefore, it would be desirable to have a wireless power supply that attaches directly to the tattoo machine, i.e. directly to the motor thereof, and which itself may be recharged with a cell phone-like USB cable. Further, it would be desirable to have a wireless power supply having up and down input buttons that, when actuated, cause more or less voltage to be transferred from the battery to the motor of the tattoo machine, which causes the motor to operate faster or slower, accordingly. In other words, the power supply presented by the present invention is both wireless and functional to operation.

SUMMARY OF THE INVENTION

A wireless power supply and voltage controller for powering and controlling a tattoo machine according to the present invention includes a battery housing having a plurality of walls that, collectively, define an interior area and a rechargeable battery positioned in the interior area of the battery housing. An input selection assembly is positioned on an exterior surface of a respective wall of the plurality of walls of the battery housing, the input selection assembly being operable to generate a speed generation signal. A controller is electrically connected to the input selection assembly that is operable to regulate a quantity of voltage flowing from the battery according to the speed generation signal.

Therefore, a general object of this invention is to provide a wireless power supply for operating and controlling voltage to a tattoo machine.

Another object of this invention is to provide a wireless power supply, as aforesaid, that is electrically and removably connected directly to the motor of a tattoo machine during use and without any wires hanging therebetween.

Still another object of this invention is to provide the wireless power supply, as aforesaid, that enables the tattoo artist to vary the speed of voltage delivered between battery and motor and, accordingly to vary the speed of the motor.

Yet another object of this invention is to provide the wireless power supply, as aforesaid, that is easy to use and economic to manufacture.

Other objects and advantages of the present invention will become apparent from the following description taken in connection with the accompanying drawings, wherein is set forth by way of illustration and example, embodiments of this invention.

BRIEF DESCRIPTION OF THE DRAWINGS

FIG. 2a is a side view of the wireless power supply as illustrated in FIG. 1a;

FIG. 2b is a side view of the wireless power supply as illustrated in FIG. 1b;

FIG. 3a is a top view of the wireless power supply according to the present invention and removed from the tattoo machine;

FIG. 3b is a side view of the wireless power supply as illustrated in FIG. 3a;

FIG. 3c is another side view of the wireless power supply as illustrated in FIG. 3a.

DESCRIPTION OF THE PREFERRED EMBODIMENT

Figure 1A:
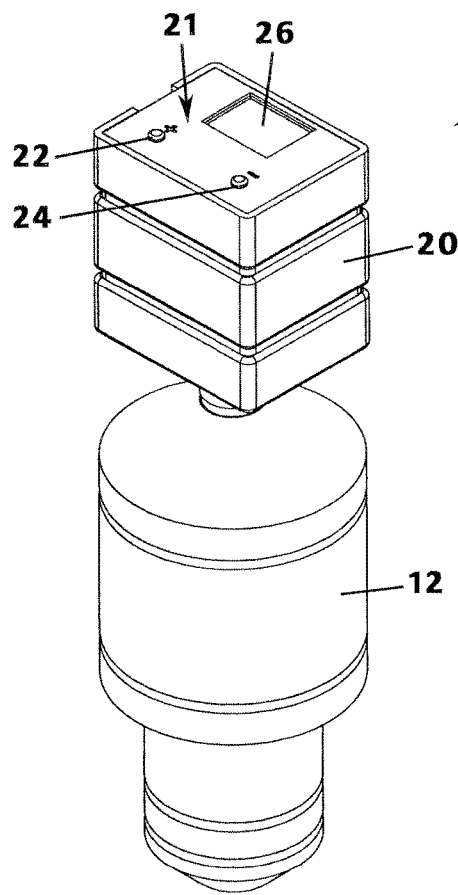
FIG. 1a is a perspective view of a wireless power supply and controller for a tattoo machine according to a preferred embodiment of the present invention, illustrated electrically connected to the tattoo machine.
Figure 1B:
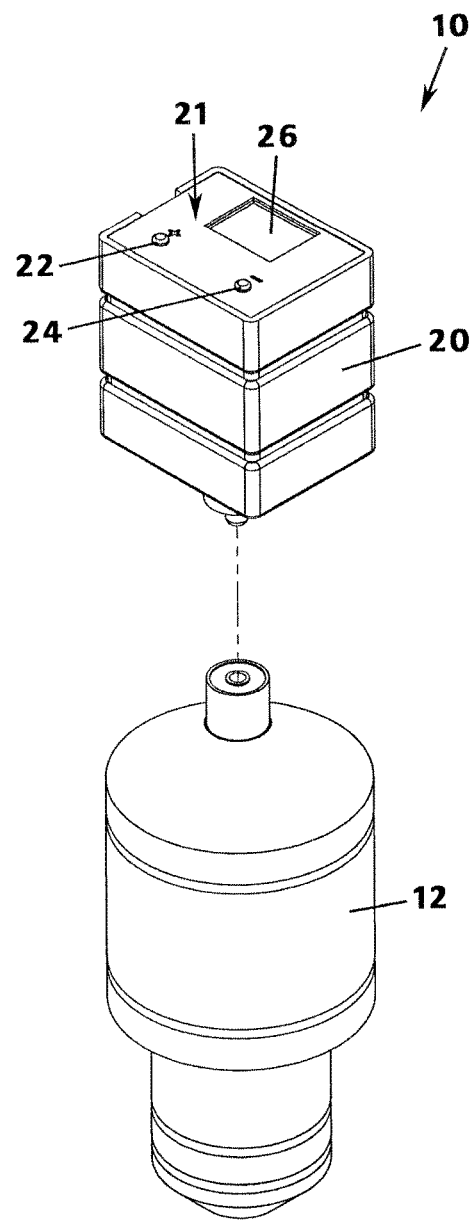
FIG. 1b is an exploded perspective view of the wireless power supply as in FIG. 1a, illustrated with the wireless power supply separated from the tattoo machine.
Figures 2A, 2B:
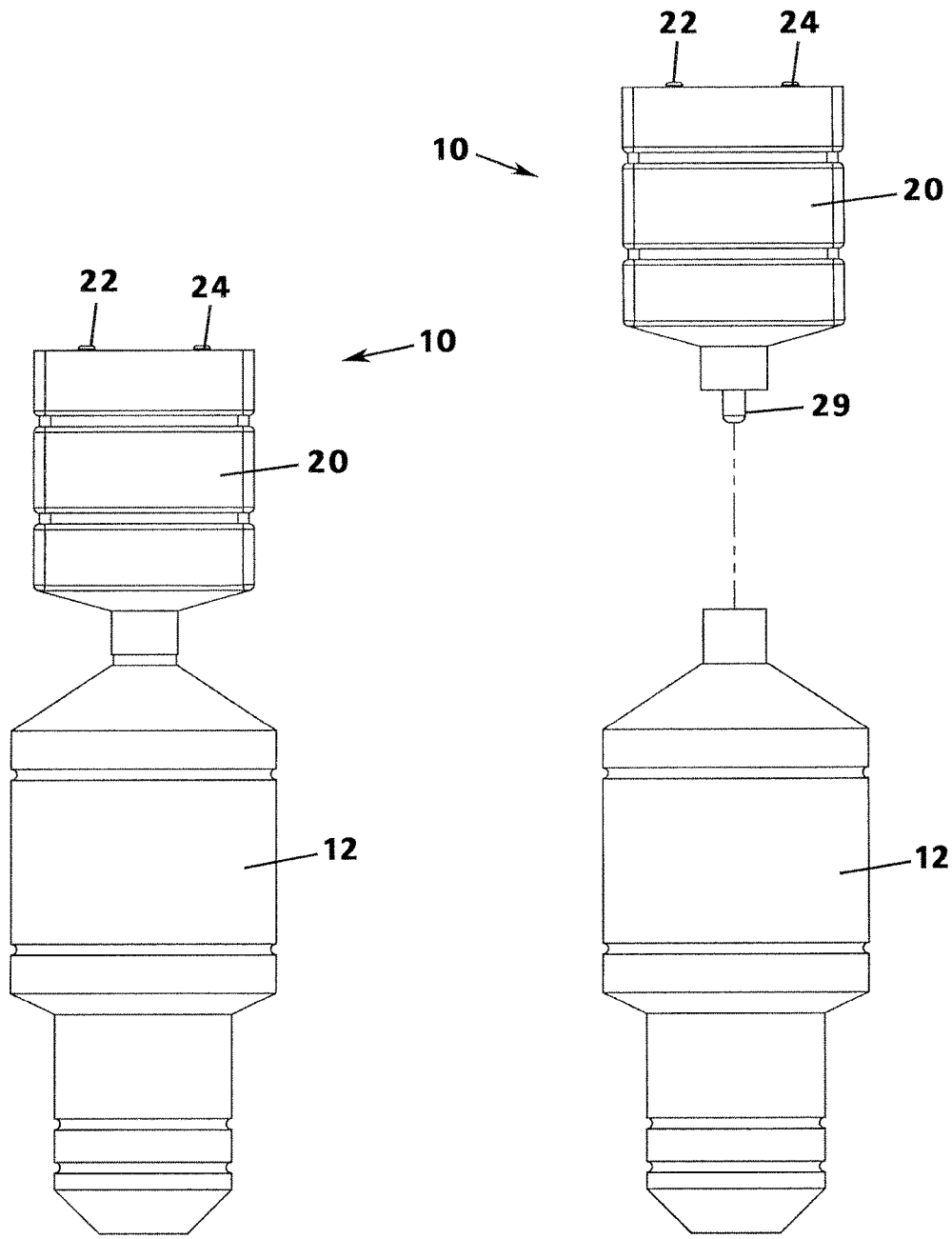
Figure 4:
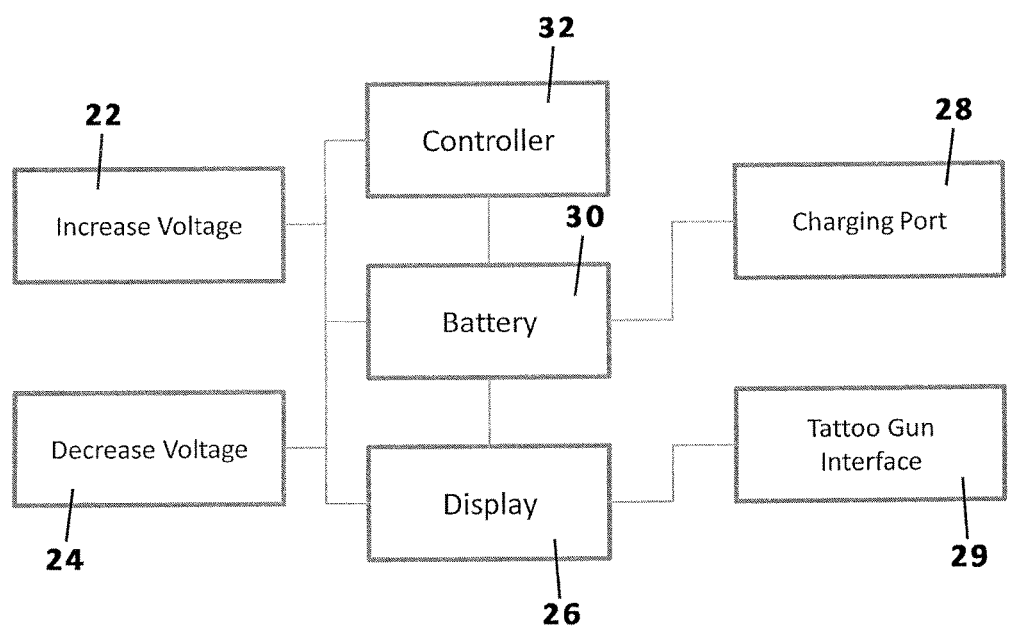
FIG. 4 is a block diagram illustrating the electronic components of the present invention.

A wireless power supply and voltage controller for a tattoo machine will be described with reference to FIGS. 1a to 4 of the accompanying drawings. More particularly, the wireless power supply 10 includes a body member having a battery housing 20 that includes a rechargeable battery 30 and which includes an up input button 22 and a down input button 24 for regulating a quantity of electrical voltage flowing to a motor of a tattoo machine.

The body member includes a battery housing 20 having a plurality of walls that enclose and define an interior area configured to hold the various electronic components that will be described below. The battery housing 20 includes a top wall on which input controls and a display 26 may be positioned.

A battery 30 is situated inside the interior area of the battery housing 20 and, preferably, is rechargeable. For instance, a USB port 28 may be mounted in a side wall of the battery housing 20 and is electrically connected to the battery 30 so that the battery may be recharged by a charger substantially similar to one used for charging a mobile phone or other rechargeable electronic device.

An input selection assembly 21 is mounted atop a wall of the battery housing 20, such as the top wall. In general, the input selection assembly 21 is electrically connected to the battery 30, is operable to adjust a quantity of voltage being transferred from the battery 30, and is the means by which a user has direct control over setting a speed of a tattoo machine 12. In an embodiment, the input selection assembly 21 includes a first input button 22 that is electrically connected to the battery 30 in a manner that decreases voltage transfer and which, in effect, results in a slower motor speed when electrically connected to the tattoo machine 12. Technically, actuation of the first input button 22 may generate an electrical speed generation signal to the battery that is indicative of decreasing voltage by a predetermined amount, such as by one-half of a volt. Similarly, the input selection assembly 21 includes a second input button 24 that is electrically connected to the battery 30 in a manner that increases voltage transfer and which, in effect, results in a faster motor speed when electrically connected to the tattoo machine 12. Technically, actuation of the second input button 24 may generate an electrical speed generation signal to the battery that is indicative of increasing voltage by a predetermined amount, such as by one-half of a volt. In actual implementation, an electronic controller 32 or pair of controllers may be electrically positioned intermediate the input selection assembly 21 and battery 30 and is operable to regulate an increase or decrease in voltage, respectively, according as may be selected by a user.

In a related aspect, the input selection assembly 21 may include a digital display 26, such as an LCD display, positioned atop the top wall proximate to the first input button 22 and second input button 24. The input buttons are electrically connected to the display 26 and the display 26 may be electrically connected to the battery 30, the display 26 being operable to publish a current voltage being delivered from the battery 30 to a motor of the tattoo machine 12.

In another aspect, the wireless power supply 10 includes an electrical interface 29 that enables connection to a motor of a tattoo machine 12. The electrical interface 29 may be an RCA plug as shown although other electronic connections are also contemplated and would also work. Specifically, the electrical interface 29 may have a first end electrically connected to the battery 30 and a second end extending away from the first end and, in fact, outside of the battery housing 20 for operable connection to the tattoo machine 12. Even more specifically, the second end is electrically connected to the first end such that electrical current from the battery 30 is electrically communicated from the battery 30 to the second end. Then, the second end is configured for mechanical coupling to (or receipt into) the tattoo machine 12, such as by friction fit or threads. As a result, electrical current and, specifically, the speed generation signal, is electrically communicated to the tattoo machine 12.

In use the battery housing 20 with a charged battery 30 may be coupled to a tattoo machine 12 via the interface 29 as discussed above. Then, the speed of the motor of the tattoo machine 12 may be adjusted using the pair of voltage input buttons.

It is understood that while certain forms of this invention have been illustrated and described, it is not limited thereto except insofar as such limitations are included in the following claims and allowable functional equivalents thereof.

The invention claimed is:

1. A wireless power supply and voltage controller for powering and controlling a tattoo machine, comprising:
   a battery housing having a plurality of walls that, collectively, define an interior area;
   a battery positioned in the interior area of said battery housing;
   an input selection assembly positioned on an exterior surface of a respective wall of said plurality of walls of said battery housing, said input selection assembly being operable to generate a speed generation signal;
   a controller electrically connected to said input selection assembly that is operable to regulate a quantity of voltage flowing from said battery according to said speed generation signal;
   an electrical interface having a first end electrically coupled to said battery and having a second end in electrical communication with said first end and extending away from said first end, said second end extending away from said battery housing and being mechanically and electrically connected to the tattoo machine for electrically communicating said speed generation signal to the tattoo machine.

2. The wireless power supply as in claim 1, wherein said electrical interface includes a RCA plug configured to selectively connect to the tattoo machine.

3. The wireless power supply as in claim 1, wherein said input selection assembly includes:
   a first input button electrically connected to said controller and operable, when actuated, to generate said speed generation signal that is indicative of a decrease in voltage;
   a second input button electrically connected to said controller and operable, when actuated, to generate said speed generation signal that is indicative of an increase in voltage.

4. The wireless power supply as in claim 3, wherein said input selection assembly includes a digital display positioned on the exterior surface of said respective wall of said battery housing, said digital display being electrically connected to said first and second input buttons and to said battery and operable to publish a selected voltage level.

5. The wireless power supply as in claim 1, further comprising a charging port mounted on a respective wall of said battery housing and electrically connected to said battery, said charging port being configured to receive a USB charging cable.

* * * * *